(12) United States Patent
Löffler et al.

(10) Patent No.: US 7,399,478 B2
(45) Date of Patent: *Jul. 15, 2008

(54) COSMETIC, PHARMACEUTICAL AND DERMATOLOGICAL PRODUCTS

(75) Inventors: Matthias Löffler, Niedernhausen (DE); Roman Morschhäuser, Mainz (DE)

(73) Assignee: Clariant Produkte (Deutschland) GmbH, Sulzbach (DE)

( * ) Notice: Subject to any disclaimer, the term of this patent is extended or adjusted under 35 U.S.C. 154(b) by 898 days.

This patent is subject to a terminal disclaimer.

(21) Appl. No.: 10/433,116

(22) PCT Filed: Nov. 28, 2001

(86) PCT No.: PCT/EP01/13867
§ 371 (c)(1), (2), (4) Date: Nov. 24, 2003

(87) PCT Pub. No.: WO02/43689
PCT Pub. Date: Jun. 6, 2002

(65) Prior Publication Data
US 2004/0109835 A1     Jun. 10, 2004

(30) Foreign Application Priority Data
Dec. 1, 2000     (DE) ................ 100 59 826

(51) Int. Cl.
A61K 8/02     (2006.01)
A61K 8/06     (2006.01)

(52) U.S. Cl. ............... 424/401; 424/400; 424/402

(58) Field of Classification Search .......... 424/401, 424/400
See application file for complete search history.

(56) References Cited

U.S. PATENT DOCUMENTS

| | | | |
|---|---|---|---|
| 3,931,089 A | 1/1976 | Karl | 260/29.65 Q |
| 4,521,578 A | 6/1985 | Chen et al. | 526/288 |
| 5,368,850 A | 11/1994 | Cauwet et al. | 424/70 |
| 5,879,718 A | 3/1999 | Sebillote-Arnaud | 424/705 |
| 5,908,618 A | 6/1999 | Lorant | 424/70.5 |
| 6,054,138 A | 4/2000 | Trebosc et al. | 424/401 |
| 6,120,780 A | 9/2000 | Dupuis et al. | 424/401 |
| 6,403,074 B1 | 6/2002 | Blankenburg et al. | |
| 6,419,912 B1 | 7/2002 | Lezer | 424/78.03 |
| 6,468,549 B1 | 10/2002 | Dupuis et al. | 424/401 |
| 6,524,564 B1 | 2/2003 | Kim et al. | 424/70.12 |
| 6,833,419 B2 * | 12/2004 | Morschhauser et al. | 526/288 |
| 6,891,011 B2 * | 5/2005 | Morschhauser et al. | 526/288 |
| 7,022,791 B2 * | 4/2006 | Loffler et al. | 526/288 |
| 7,186,405 B2 * | 3/2007 | Loffler et al. | 424/65 |
| 7,186,774 B2 * | 3/2007 | Morschhauser et al. | 524/555 |

FOREIGN PATENT DOCUMENTS

| | | |
|---|---|---|
| CA | 2363079 | 8/2000 |
| EP | 0 356 241 | 2/1990 |
| EP | 0 815 828 | 1/1998 |
| EP | 0 815 844 | 1/1998 |
| EP | 0 815 845 | 1/1998 |
| EP | 0 850 642 | 7/1998 |
| FR | 2 791 558 | 10/2000 |
| WO | WO 99/04750 | 2/1999 |
| WO | WO 00/12588 | 3/2000 |

OTHER PUBLICATIONS

Co-pending U.S. Appl. No. 10/433,117, 10/433,112, 10/433,204, 10/433,175, 10/433,113, 10/433,203, 10/433,120, 10/433,118, 10/433,199, 10/433,006, 10/433,179, 10/433,119.*
English Translation of PCT IPER for PCT/EP01/13867, Dated Feb. 26, 2003.
English abstract for JP 58-099407, "Surfactant-free emulsion cosmetics—comprising water, oil component and emulsion and consisting of water-insoluble and water absorbable polymer", Sep. 25, 1993.

* cited by examiner

Primary Examiner—M P Woodward
Assistant Examiner—M. S. Mercier
(74) Attorney, Agent, or Firm—Richard P. Silverman

(57) ABSTRACT

The invention provides cosmetic, pharmaceutical and dermatological compositions comprising at least one copolymer obtainable by free-radical copolymerization of
  A) acryloyldimethyltaurine and/or acryloyldimethyltaurates,
  B) if desired, one or more further olefinically unsaturated, noncationic comonomers,
  C) if desired, one or more olefinically unsaturated, cationic comonomers,
  D) if desired, one or more silicon-containing components,
  E) if desired, one or more fluorine-containing components,
  F) if desired, one or more macromonomers,
  G) the copolymerization taking place if desired in the presence of at least one polymeric additive,
  H) with the proviso that component A) is copolymerized with at least one component selected from one of the groups D) to G).

21 Claims, No Drawings

COSMETIC, PHARMACEUTICAL AND DERMATOLOGICAL PRODUCTS

The present invention relates to cosmetic, pharmaceutical, and dermatological compositions comprising comb copolymers based on acryloyldimethyltaurine.

Consumer desires and cosmetic product rheology are closely interlinked. Thus, for example, the visual appearance of a cream or lotion is influenced by the viscosity. The sensorial properties, such as consistency or spreadability, determine the individual profile of a cosmetic product. The effectiveness of active substances (e.g., sun protection filters) and the storage stability of the formulation are also closely related to the rheological properties of the products.

In the cosmetics sector a leading part is played by polyelectrolytes as thickeners and gel formers. State of the art are, in particular, thickeners based on poly(meth)acrylic acid and the water-soluble copolymers thereof. The diversity of the possible structures and the diverse possibilities for use associated therewith are manifested not least in a multiplicity of patents filed worldwide since the mid-1970s.

A substantial drawback of the thickeners based on poly(meth)acrylic acid is the heavy pH dependency of the thickening action. Thus, in general, a sufficiently high viscosity is only developed when the pH of the formulation is adjusted to a level of more than 6, i.e., the poly(meth)acrylic acid is in neutralized form. Furthermore, the corresponding compositions are sensitive to UV radiation and also to shearing, and they also impart a sticky feeling on the skin. The handling of such thickeners is also problematic. Since the thickeners are generally in acidic form, formulation involves an additional neutralizing step.

In the 1990s, innovative thickeners based on crosslinked and neutralized polyacryloyldimethyltaurates were introduced into the market (EP-B-0 815 828, EP-B-0 815 844, EP-B-0 815 845 and EP-A-0 850 642). Both in the form of the preneutralized homopolymer and as the corresponding copolymer (®ARISTOFLEX AVC, CLARIANT GmbH), these thickeners are superior in many respects to the poly(meth)acrylate products. For example, acryloyldimethyltaurate-based thickener systems exhibit outstanding properties in pH ranges below 6, i.e., in a pH range in which it is no longer possible to operate with conventional poly(meth)acrylate thickeners. High UV and shear stability, outstanding viscoelastic properties, great ease of processing, and a favorable toxicological profile of the principal monomer make acryloyldimethyltaurate-based thickener systems new, modern representatives with a high potential for the future.

Over the course of recent years a further thickener concept has become established on the market. By hydrophobic modification of conventional poly(meth)acrylates, an access route has been found here to polymers which have both thickening and emulsifying/dispersing properties. Examples of commercial hydrophobically modified poly(meth)acrylates are ®PEMULEN TR-1 and TR-2 from BF Goodrich and ®ACU-LYN 22, Rohm & Haas. Since these hydrophobically modified polymers are constructed on the basis of (meth)acrylic acid, they also possess the abovementioned disadvantages of the poly(meth)acrylates.

Surprisingly it has now been found that a new class of comb polymers based on acryloyldimethyltaurine (AMPS)—and suitable in the capacity of a thickener, bodying agent, emulsifier, solubilizer, dispersant, lubricant, adhesive, conditioner and/or stabilizer—are outstandingly suitable for the formulation of cosmetic, pharmaceutical, and dermatological compositions.

The invention accordingly provides cosmetic, pharmaceutical, and dermatological compositions comprising at least one copolymer obtainable by free-radical copolymerization of
A) acryloyldimethyltaurine and/or acryloyldimethyltaurates,
B) if desired, one or more further olefinically unsaturated, noncationic, optionally crosslinking comonomers which have at least one oxygen, nitrogen, sulfur or phosphorus atom and possess a molecular weight of less than 500 g/mol,
C) if desired, one or more olefinically unsaturated, cationic comonomers which have at least one oxygen, nitrogen, sulfur or phosphorus atom and possess a molecular weight of less than 500 g/mol,
D) if desired, one or more silicon-containing components capable of free-radical polymerization and having a functionality of at least one,
E) if desired, one or more fluorine-containing components capable of free-radical polymerization and having a functionality of at least one,
F) if desired, one or more olefinically mono- or polyunsaturated, optionally crosslinking macromonomers each possessing at least one oxygen, nitrogen, sulfur or phosphorus atom and having a number-average molecular weight of greater than or equal to 200 g/mol, the macromonomers not being a silicon-containing component D) or fluorine-containing component E),
G) the copolymerization taking place if desired in the presence of at least one polymeric additive having number-average molecular weights of from 200 g/mol to $10^9$ g/mol,
H) with the proviso that component A) is copolymerized with at least one component selected from one of the groups D) to G).

The copolymers of the invention preferably possess a molecular weight of from $10^3$ g/mol to $10^9$ g/mol, more preferably from $10^4$ to $10^7$ g/mol, with particular preference from $5*10^4$ to $5*10^6$ g/mol.

The acryloyldimethyltaurates can be the organic or inorganic salts of acryloyldimethyltaurine (acrylamidopropyl-2-methyl-2-sulfonic acid). Preference is given to the $Li^+$, $Na^+$, $K^+$, $Mg^{++}$, $Ca^{++}$, $Al^{+++}$ and/or $NH_4^+$ salts. Likewise preferred are the monoalkylammonium, dialkylammonium, trialkylammonium and/or tetraalkylammonium salts, in which the alkyl substituents of the amines may independently of one another be $(C_1-C_{22})$-alkyl radicals or $(C_2-C_{10})$-hydroxyalkyl radicals. Preference is also given to mono- to triethoxylated ammonium compounds with different degrees of ethoxylation. It should be noted that mixtures of two or more of the abovementioned representatives are also embraced by the invention.

The degree of neutralization of the acryloyldimethyltaurine can be between 0 and 100%, with particular preference being given to a degree of neutralization of more than 80%.

Based on the total mass of the copolymers, the amount of acryloyldimethyltaurine and/or acryloyldimethyltaurates is at least 0.1% by weight, preferably from 20 to 99.5% by weight, more preferably from 50 to 98% by weight.

As comonomers B) it is possible to use all olefinically unsaturated noncationic monomers whose reaction parameters allow copolymerization with acryloyldimethyltaurine and/or acryloyldimethyltaurates in the respective reaction media. Preferred comonomers B) are unsaturated carboxylic acids and their anhydrides and salts, and also their esters with aliphatic, olefinic, cycloaliphatic, arylaliphatic or aromatic alcohols having a carbon number of from 1 to 30.

Particularly preferred unsaturated carboxylic acids are acrylic acid, methacrylic acid, styrenesulfonic acid, maleic acid, fumaric acid, crotonic acid, itaconic acid, and senecic acid.

Preferred counterions are Li$^+$, Na$^+$, K$^+$, Mg$^{++}$, Ca$^{++}$, Al$^{+++}$, NH$_4^+$, monoalkylammonium, dialkylammonium, trialkylammonium and/or tetraalkylammonium radicals, in which the alkyl substituents of the amines independently of one another can be (C$_1$-C$_{22}$)-alkyl radicals or (C$_2$-C$_{10}$)-hydroxyalkyl radicals. It is additionally possible to employ mono- to triethoxylated ammonium compounds with a different degree of ethoxylation. The degree of neutralization of the carboxylic acids can be between 0 and 100%.

Further preferred comonomers B) are open-chain N-vinyl amides, preferably N-vinylformamide (VIFA), N-vinylmethylformamide, N-vinylmethylacetamide (VIMA) and N-vinylacetamide; cyclic N-vinyl amides (N-vinyl lactams) with a ring size of 3 to 9, preferably N-vinylpyrrolidone (NVP) and N-vinylcaprolactam; amides of acrylic and methacrylic acid, preferably acrylamide, methacrylamide, N,N-dimethylacrylamide, N,N-diethylacrylamide, and N,N-diisopropylacrylamide; alkoxylated acrylamides and methacrylamides, preferably hydroxyethyl methacrylate, hydroxymethylmethacrylamide, hydroxyethylmethacrylamide, hydroxypropylmethacrylamide, and mono [2-(methacryloyloxy)ethyl]succinate; N,N-dimethylamino methacrylate; diethylaminomethyl methacrylate; acrylamido- and methacrylamido-glycolic acid; 2- and 4-vinylpyridine; vinyl acetate; glycidyl methacrylate; styrene; acrylonitrile; vinyl chloride; stearyl acrylate; lauryl methacrylate; vinylidene chloride; and/or tetrafluoroethylene.

Likewise suitable comonomers B) are inorganic acids and their salts and esters. Preferred acids are vinylphosphonic acid, vinylsulfonic acid, allylphosphonic acid, and methallylsulfonic acid.

The weight fraction of the comonomers B), based on the total mass of the copolymers, can be from 0 to 99.8% by weight and is preferably from 0.5 to 80% by weight, more preferably from 2 to 50% by weight.

Suitable comonomers C) include all olefinically unsaturated monomers with cationic charge which are capable of forming copolymers with acryloyldimethyltaurine or its salts in the chosen reaction media. The resulting distribution of the cationic charges across the chains can be random, alternating, blocklike or gradientlike. It may be noted that the cationic comonomers C) also comprehend those which bear the cationic charge in the form of a betaine, zwitterionic or amphoteric structure.

Comonomers C) for the purposes of the invention are also amino-functionalized precursors which can be converted by polymer-analogous reactions into their corresponding quaternary derivatives (e.g., reaction with dimethyl sulfate, methyl chloride), zwitterionic derivatives (e.g., reaction with hydrogen peroxide), betaine derivatives (e.g., reaction with chloroacetic acid), or amphoteric derivatives.

Particularly preferred comonomers C) are
diallyldimethylammonium chloride (DADMAC),
[2-(methacryloyloxy)ethyl]trimethylammonium chloride (MAPTAC),
[2-(acryloyloxy)ethyl]trimethylammonium chloride,
[2-methacrylamidoethyl]trimethylammonium chloride,
[2-(acrylamido)ethyl]trimethylammonium chloride,
N-methyl-2-vinylpyridinium chloride,
N-methyl-4-vinylpyridinium chloride,
dimethylaminoethyl methacrylate,
dimethylaminopropylmethacrylamide,
methacryloylethyl N-oxide and/or
methacryloylethylbetaine.

The weight fraction of the comonomers C), based on the total mass of the copolymers, can be from 0.1 to 99.8% by weight, more preferably from 0.5 to 30% by weight, and very preferably from 1 to 20% by weight. Suitable polymerizable silicon-containing components D) are all compounds which are olefinically at least monounsaturated and capable of free-radical copolymerization under the reaction conditions chosen in each case. The distribution of the individual silicone-containing monomers across the polymer chains which form need not necessarily be random. The invention also embraces the formation, for example, of blocklike (including multiblock) or gradientlike structures. Combinations of two or more different silicone-containing representatives are also possible. The use of silicone-containing components having two or more polymerization-active groups leads to the construction of branched or crosslinked structures.

Preferred silicone-containing components are those of formula (I).

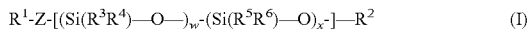

$$R^1\text{-}Z\text{-}[(Si(R^3R^4)\text{—}O\text{—})_w\text{-}(Si(R^5R^6)\text{—}O)_x\text{-}]\text{—}R^2 \qquad (I)$$

In this formula R$^1$ represents a polymerizable function from the group of the vinylically unsaturated compounds which is suitable for the synthesis of polymeric structures by a free-radical route. R$^1$ represents preferably a vinyl, allyl, methallyl, methylvinyl, acryloyl (CH$_2$=CH—CO—), methacryloyl (CH$_2$=C[CH$_3$]—CO—), crotonyl, senecionyl, itaconyl, maleyl, fumaryl or styryl radical.

The attachment of the silicone-containing polymer chain to the reactive end group R$^1$ requires a suitable chemical bridge Z. Preferred bridges Z are —O—, ((C$_1$-C$_{50}$)alkylene), -((C$_6$-C$_{30}$)arylene)-, -((C$_5$-C$_8$)cycloalkylene)-, -((C$_1$-C$_{50}$)alkenylene)-, -(polypropylene oxide)$_n$-, -(polyethylene oxide)$_o$-, -(polypropylene oxide)$_n$(polyethylene oxide)$_o$-, where n and o independently of one another denote numbers from 0 to 200 and the distribution of the EO/PO units can be random or in the form of blocks. Further suitable bridge groups Z are -((C$_1$-C$_{10}$)alkyl)-(Si(OCH$_3$)$_2$)— and —(Si(OCH$_3$)$_2$)—.

The polymeric central moiety is represented by silicone-containing repeating units. The radicals R$^3$, R$^4$, R$^5$, and R$^6$ denote independently of one another —CH$_3$, —O—CH$_3$, —C$_6$H$_5$ or —O—C$_6$H$_5$.

The indices w and x represent stoichiometric coefficients which amount independently of one another to from 0 to 500, preferably 10 to 250.

The distribution of the repeating units across the chain can be not only purely random but also blocklike, alternating or gradientlike.

R$^2$ can first be an aliphatic, olefinic, cycloaliphatic, arylaliphatic or aromatic (C$_1$-C$_{50}$) hydrocarbon radical (linear or branched) or —OH, —NH$_2$, —N(CH$_3$)$_2$, —R$^7$ or stand for the structural unit [-Z-R$^1$]. The definition of the two variables Z and R$^1$ has already been explained. R$^7$ stands for further Si-containing groups. Preferred radicals R$^7$ are —O—Si(CH$_3$)$_3$, —O—Si(Ph)$_3$, —O—Si(O—Si(CH$_3$)$_3$)$_2$CH$_3$), and —O—Si(O—Si(Ph)$_3$)$_2$Ph). If R$^2$ is an element of the group [-Z-R$^1$] the monomers in question are difunctional monomers which can be used to crosslink the polymer structures which form. Formula (I) describes not only silicone-containing polymer species with vinylic functionalization and a polymer-typical distribution, but also defined compounds having discrete molecular weights.

Particularly preferred silicone-containing components are the following components with acrylic or methacrylic modification:

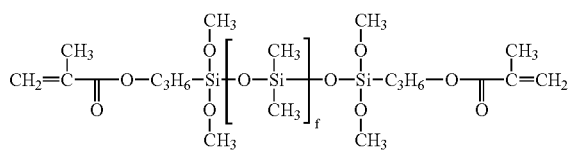

methacryloyloxypropyldimethylsilyl-endblocked polydimethylsiloxanes (f=2 to 500)

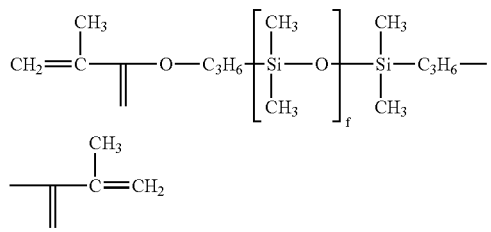

methacryloyloxypropyl-endblocked polydimethylsiloxanes (f=2 to 500)

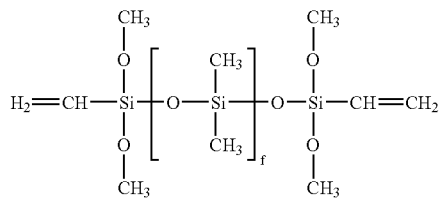

vinyldimethoxysilyl-endblocked polydimethylsiloxanes (f=2-500)

Based on the total mass of the copolymers, the amount of silicon-containing components can be up to 99.9% by weight, preferably from 0.5 to 30% by weight, more preferably from 1 to 20% by weight.

Suitable polymerizable fluorine-containing components E) include all compounds which are olefinically at least monounsaturated and which are capable of free-radical copolymerization under the reaction conditions chosen in each case. The distribution of the individual fluorine-containing monomers across the polymer chains which form need not necessarily be random. The invention also embraces the formation of blocklike (including multiblock) or gradientlike structures, for example. Combinations of two or more different fluorine-containing components E) are also possible, it being clear to the expert that monofunctional representatives lead to the formation of comb-shaped structures while di-, tri-, or polyfunctional components E) lead to structures which are at least partly crosslinked.

Preferred fluorine-containing components E) are those of formula (II).

$$R^1—Y—C_rH_2rC_sF_{2s}CF_3 \quad (II)$$

In this formula $R^1$ represents a polymerizable function from the group of the vinylically unsaturated compounds which is suitable for the construction of polymeric structures by a free-radical route. $R^1$ is preferably a vinyl, allyl, methallyl, methylvinyl, acryloyl ($CH_2$=CH—CO—), methacryloyl ($CH_2$=C[$CH_3$]—CO—), crotonyl, senecionyl, itaconyl, maleyl, fumaryl or styryl radical, more preferably an acryloyl or methacryloyl radical.

The attachment of the fluorine-containing group to the reactive end group $R^1$ requires a suitable chemical bridge Y. Preferred bridges Y are —O—, —C(O)—, —C(O)—O—, —S—, —O—$CH_2$—CH(O—)—$CH_2$OH, —O—$CH_2$—CH(OH)—$CH_2$—O—, —O—$SO_2$—O—, —O—S(O)—O—, —PH—, —P($CH_3$)—, —$PO_3$—, —NH—, —N($CH_3$)—, —O-($C_1$-$C_{50}$)alkyl-O—, —O-phenyl-O—, —O-benzyl-O—, —O-($C_5$-$C_8$)cycloalkyl-O—, —O-($C_1$-$C_{50}$)alkenyl-O—, —O—(CH($CH_3$)—$CH_2$—O)$_n$—, —O—($CH_2$—$CH_2$—O)$_n$-, and —O—([CH—$CH_2$—O]$_n$-[$CH_2$—$CH_2$—O]$_m$)$_o$-, where n, m, and o independently of one another denote numbers from 0 to 200 and the distribution of the EO and PO units can be random or in the form of blocks. r and s are stoichiometric coefficients which independently of one another denote numbers from 0 to 200.

Preferred fluorine-containing components E) of formula (II) are
perfluorohexylethanol methacrylate,
perfluorohexoylpropanol methacrylate,
perfluoroctylethanol methacrylate,
perfluoroctylpropanol methacrylate,
perfluorohexylethanolyl polyglycol ether methacrylate,
perfluorohexoylpropanolyl poly[ethylglycol-co-propylene glycol ether]acrylate,
perfluoroctylethanolyl poly[ethylglycol-block-co-propylene glycol ether]methacrylate,
perfluoroctylpropanolyl polypropylene glycol ether methacrylate.

Based on the total mass of the copolymers the amount of fluorine-containing components can be up to 99.9% by weight, preferably from 0.5 to 30% by weight, more preferably from 1 to 20% by weight.

The macromonomers F) are at least singly olefinically functionalized polymers having one or more discrete repeating units and a number-average molecular weight of greater than or equal to 200 g/mol. In the copolymerization it is also possible to use mixtures of chemically different macromonomers F). The macromonomers are polymeric structures composed of one or more repeating units and have a molecular weight distribution characteristic of polymers.

Preferred macromonomers F) are compounds of formula (III).

$$R^1—Y—[(A)_v-(B)_w-(C)_x-(D)_z]—R^2 \quad (III)$$

$R^1$ represents a polymerizable function from the group of the vinylically unsaturated compounds which are suitable for constructing polymeric structures by a free-radical route. Preferably $R^1$ is a vinyl, allyl, methallyl, methylvinyl, acryloyl ($CH_2$=CH—CO—), methacryloyl ($CH_2$=C[$CH_3$]—CO—), crotonyl, senecionyl, itaconyl, maleyl, fumaryl or styryl radical.

Attachment of the polymer chain to the reactive end group requires a suitable bridging group Y. Preferred bridges Y are —O—, —C(O)—, —C(O)—O—, —S—, —O—$CH_2$—CH(O—)—$CH_2$OH, —O—$CH_2$—CH(OH)—$CH_2$O—, —O—$SO_2$—O—, —O—$SO_2$—O—, —O—SO—O—, —PH—, —P($CH_3$)—, —$PO_3$—, —NH—, and —N($CH_3$)—, more preferably —O—.

The polymeric central moiety of the macromonomer is represented by the discrete repeating units A, B, C, and D. Preferably the repeating units A, B, C, and D are derived from: acrylamide, methacrylamide, ethylene oxide, propylene oxide, AMPS, acrylic acid, methacrylic acid, methyl methacrylate, acrylonitrile, maleic acid, vinyl acetate, styrene, 1,3-butadiene, isoprene, isobutene, diethylacrylamide, and diisopropylacrylamide.

The indices v, w, x, and z in formula (III) represent the stoichiometric coefficients relating to the repeating units A, B, C, and D. v, w, x, and z amount independently of one another to from 0 to 500, preferably 1 to 30, it being necessary for the sum of the four coefficients on average to be $\geq 1$.

The distribution of the repeating units over the macromonomer chain can be random, blocklike, alternating or gradientlike.

$R^2$ denotes a linear or branched aliphatic, olefinic, cycloaliphatic, arylaliphatic or aromatic ($C_1$-$C_{50}$) hydrocarbon radical, OH, —$NH_2$, —$N(CH_3)_2$ or is the structural unit [—Y—$R^1$].

In the case of $R^2$ being [—Y—$R^1$] the macromonomers in question are difunctional and suitable for crosslinking the copolymers.

Particularly preferred macromonomers F) are acrylically or methacrylically monofunctionalized alkyl ethoxylates of formula (IV).

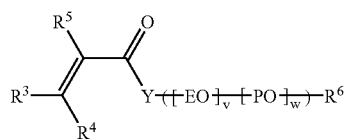

$R_3$, $R_4$, $R_5$, and $R_6$ are independently of one another hydrogen or n-aliphatic, iso-aliphatic, olefinic, cycloaliphatic, arylaliphatic or aromatic ($C_1$-$C_{30}$) hydrocarbon radicals.

Preferably $R_3$ and $R_4$ are H or —$CH_3$, more preferably H; $R_5$ is H or —$CH_3$; and $R_6$ is an n-aliphatic, iso-aliphatic, olefinic, cycloaliphatic, arylaliphatic or aromatic ($C_1$-$C_{30}$) hydrocarbon radical.

v and w are in turn the stoichiometric coefficients relating to the ethylene oxide units (EO) and propylene oxide units (PO). v and w amount independently of one another to from 0 to 500, preferably 1 to 30, it being necessary for the sum of v and w to be on average $\geq 1$. The distribution of the EO and PO units over the macromonomer chain can be random, blocklike, alternating or gradientlike. Y stands for the above-mentioned bridges.

Further particularly preferred macromonomers F) have the following structure in accordance with formula (IV):

| Name | $R^3$ | $R^4$ | $R^5$ | $R^6$ | v | w |
|---|---|---|---|---|---|---|
| ® LA-030 methacrylate | H | H | —$CH_3$ | -lauryl | 3 | 0 |
| ® LA-070 methacrylate | H | H | —$CH_3$ | -lauryl | 7 | 0 |
| ® LA-200 methacrylate | H | H | —$CH_3$ | -lauryl | 20 | 0 |
| ® LA-250 methacrylate | H | H | —$CH_3$ | -lauryl | 25 | 0 |
| ® T-080 methacrylate | H | H | —$CH_3$ | -talc | 8 | 0 |
| ® T-080 acrylate | H | H | H | -talc | 8 | 0 |
| ® T-250 methacrylate | H | H | —$CH_3$ | -talc | 25 | 0 |
| ® T-250 crotonate | —$CH_3$ | H | —$CH_3$ | -talc | 25 | 0 |
| ® OC-030 methacrylate | H | H | —$CH_3$ | -octyl | 3 | 0 |
| ® OC-105 methacrylate | H | H | —$CH_3$ | -octyl | 10 | 5 |
| ® Behenyl-010-methylaryl | H | H | H | -behenyl | 10 | 0 |
| ® Behenyl-020-methylaryl | H | H | H | -behenyl | 20 | 0 |
| ® Behenyl-010-senecionyl | —$CH_3$ | —$CH_3$ | H | -behenyl | 10 | 0 |
| ® PEG-440 diacrylate | H | H | H | -acryloyl | 10 | 0 |
| ® B-11-50 methacrylate | H | H | —$CH_3$ | -butyl | 17 | 13 |
| ® MPEG-750 methacrylate | H | H | —$CH_3$ | -methyl | 18 | 0 |
| ® P-010 acrylate | H | H | H | -phenyl | 10 | 0 |
| ® O-050 acrylate | H | H | H | -oleyl | 5 | 0 |

Further particularly suitable macromonomers F) are esters of (meth)acrylic acid with ($C_{10}$-$C_{18}$) fatty alcohol polyglycol ethers having 8 EO units (Genapol® C-080)

$C_{11}$ oxo alcohol polyglycol ethers having 8 EO units (Genapol® UD-080)

($C_{12}$-$C_{14}$) fatty alcohol polyglycol ethers having 7 EO units (Genapol® LA-070)

($C_{12}$-$C_{14}$) fatty alcohol polyglycol ethers having 11 EO units (Genapol® LA-110)

($C_{16}$-$C_{18}$) fatty alcohol polyglycol ethers having 8 EO units (Genapol® T-080)

($C_{16}$-$C_{18}$) fatty alcohol polyglycol ethers having 15 EO units (Genapol® T-150)

($C_{16}$-$C_{18}$) fatty alcohol polyglycol ethers having 11 EO units (Genapol® T-110)

($C_{16}$-$C_{18}$) fatty alcohol polyglycol ethers having 20 EO units (Genapol® T-200)

($C_{16}$-$C_{18}$) fatty alcohol polyglycol ethers having 25 EO units (Genapol® T-250)

($C_{18}$-$C_{22}$) fatty alcohol polyglycol ethers having 25 EO units and/or iso-($C_{16}$-$C_{18}$) fatty alcohol polyglycol ethers having 25 EO units.

The Genapol® grades are products of Clariant GmbH.

The molecular weight of the macromonomers F) is preferably from 200 g/mol to $10^6$ g/mol, more preferably from 150 to $10^4$ g/mol, and very preferably from 200 to 5 000 g/mol.

Based on the total mass of the copolymers it is possible to use suitable macromonomers at up to 99.9% by weight. The ranges used are preferably from 0.5 to 30% by weight and from 70 to 99.5% by weight. Particularly preferred are fractions of from 1 to 20% by weight and from 75 to 95% by weight.

Preferred copolymers are those obtainable by copolymerizing at least components A), C) and D).

Further preferred copolymers are those obtainable by copolymerizing at least components A), C) and E).

Further preferred copolymers are those obtainable by copolymerizing at least components A), D) and F).

Further preferred copolymers are those obtainable by copolymerizing at least components A) and F).

In one preferred embodiment the copolymerization is conducted in the presence of at least one polymeric additive G), the additive G) being added wholly or partly in solution to the polymerization medium before the actual copolymerization. The use of two or more additives G) is likewise in accordance with the invention.

Crosslinked additives G) may likewise be used.

The additives G) or mixtures thereof must only be wholly or partly soluble in the chosen polymerization medium. During the actual polymerization step the additive G) has a number of functions. On the one hand it prevents the formation of overcrosslinked polymer fractions in the copolymer which forms in the actual polymerization step, and on the other hand the additive G) is statistically attacked by active free radicals in accordance with the very well-known mechanism of graft copolymerization. Depending on the particular additive G), this results in greater or lesser fractions of the additive being incorporated into the copolymers. Moreover, suitable additives G) possess the property of altering the solution parameters of the copolymers which form during the free-radical polymerization reaction in such a way that the average molecular weights are shifted to higher values. As compared with analogous copolymers prepared without the addition of the additives G), those prepared with the addition of additives G) advantageously exhibit a significantly higher viscosity in aqueous solution.

Preferred additives G) are homopolymers and copolymers which are soluble in water and/or alcohols, preferably in t-butanol. The term "copolymers" also comprehends those having more than two different monomer types.

Particularly preferred additives G) are homopolymers and copolymers of N-vinylformamide, N-vinylacetamide, N-vinylpyrrolidone, ethylene oxide, propylene oxide, acryloyldimethyltaurine, N-vinylcaprolactam, N-vinylmethylacetamide, acrylamide, acrylic acid, methacrylic acid, N-vinylmorpholide, hydroxyethyl methacrylate, diallyldimethylammonium chloride (DADMAC) and/or [2-(methacryloyloxy)ethyl]-trimethylammonium chloride (MAPTAC); polyalkylene glycols and/or alkylpolyglycols.

Particularly preferred additives G) are polyvinylpyrrolidones (e.g., Luviskol K15®, K20® and K30® from BASF), poly(N-vinylformamides), poly(N-vinylcaprolactams), and copolymers of N-vinylpyrrolidone, N-vinylformamide and/or acrylic acid, which may also have been partly or fully hydrolyzed.

The molecular weight of the additives G) is preferably from $10^2$ to $10^7$ g/mol, more preferably from $0.5*10^4$ to $10^6$ g/mol.

The amount in which the polymeric additive G) is used, based on the total mass of the monomers to be polymerized during the copolymerization, is preferably from 0.1 to 90% by weight, more preferably from 1 to 20% by weight, and with particular preference from 1.5 to 10% by weight.

In another preferred embodiment the copolymers of the invention are crosslinked, i.e., they contain comonomers having at least two polymerizable vinyl groups. Preferred crosslinkers are methylenebisacrylamide; methylenebismethacrylamide; esters of unsaturated monocarboxylic and polycarboxylic acids with polyols, preferably diacrylates and triacrylates, dimethacrylates and trimethacrylates, more preferably butanediol and ethylene glycol diacrylate and methacrylate, trimethylolpropane triacrylate (TMPTA) and trimethylolpropane trimethacrylate (TMPTMA); allyl compounds, preferably allyl (meth)acrylate, triallyl cyanurate, diallyl maleate, polyallyl esters, tetraallyloxyethane, triallylamine, tetraallylethylenediamine; allyl esters of phosphoric acid; and/or vinylphosphonic acid derivatives. A particularly preferred crosslinker is trimethylolpropane triacrylate (TMPTA). The weight fraction of crosslinking comonomers, based on the total mass of the copolymers, is preferably up to 20% by weight, more preferably from 0.05 to 10% by weight, and very preferably from 0.1 to 7% by weight.

The polymerization medium used may comprise all organic or inorganic solvents which have a very substantially inert behavior with respect to free-radical polymerization reactions and which advantageously allow the formation of medium or high molecular weights. Those used preferably include water; lower alcohols; preferably methanol, ethanol, propanols, iso-, sec- and t-butanol, very preferably t-butanol; hydrocarbons having 1 to 30 carbon atoms, and mixtures of the aforementioned compounds.

The polymerization reaction takes place preferably in the temperature range between 0 and 150° C., more preferably between 10 and 100° C., either at atmospheric pressure or under elevated or reduced pressure. If desired the polymerization may also be performed under an inert gas atmosphere, preferably under nitrogen.

In order to initiate the polymerization it is possible to use high-energy electromagnetic rays, mechanical energy, or the customary chemical polymerization initiators, such as organic peroxides, e.g., benzoyl peroxide, tert-butyl hydroperoxide, methyl ethyl ketone peroxide, cumene hydroperoxide, dilauroyl peroxide or azo initiators, such as azodiisobutyronitrile (AIBN), for example. Likewise suitable are inorganic peroxy compounds, such as $(NH_4)_2S_2O_8$, $K_2S_2O_8$ or $H_2O_2$, for example, where appropriate in combination with reducing agents (e.g., sodium hydrogensulfite, ascorbic acid, iron(II) sulfate, etc.) or redox systems comprising as reducing component an aliphatic or aromatic sulfonic acid (e.g., benzenesulfonic acid, toluenesulfonic acid, etc.).

Serving as the polymerization medium may be any solvents which are very substantially inert in respect of free-radical polymerization reactions and which allow the development of high molecular weights. Use is preferably made of water and lower, tertiary alcohols or hydrocarbons having 3 to 30 carbon atoms. In one particularly preferred embodiment t-butanol is used as the reaction medium. Mixtures of two or more representatives of the potential solvents described are of course likewise in accordance with the invention. This also includes emulsions of mutually immiscible solvents (e.g., water/hydrocarbons). In principle, all kinds of reaction regime leading to the polymer structures of the invention are suitable (solution polymerization, emulsion methods, precipitation methods, high-pressure methods, suspension methods, bulk polymerization, gel polymerization, and so on). Preferred suitability is possessed by precipitation polymerization, particularly preferred suitability by precipitation polymerization in tert-butanol.

The following list shows 67 copolymers with particular suitability for formulating the compositions of the invention. The different copolymers 1 to 67 are obtainable in accordance with the following preparation processes 1, 2, 3, and 4.

Process 1:

These polymers can be prepared by the precipitation method in tert-butanol. The monomers were introduced in t-butanol, the reaction mixture was rendered inert, and then, after initial heating to 60° C., the reaction was initiated by addition of the corresponding t-butanol-soluble initiator (preferably dilauroyl peroxide). After the end of reaction (2 hours) the polymers were isolated by removal of the solvent under suction and by subsequent vacuum drying.

Process 2:

These polymers are preparable by the gel polymerization method in water. The monomers are dissolved in water, the reaction mixture is rendered inert, and then, after initial heating to 65° C., the reaction is initiated by addition of suitable initiators or initiator systems (preferably $Na_2S_2O_8$). The polymer gels are subsequently comminuted and the polymers are isolated after drying.

Process 3:

These polymers are preparable by the emulsion method in water. The monomers are emulsified in a mixture of water/organ. solvent (preferably cyclohexane) using an emulsifier, the reaction mixture is rendered inert by means of $N_2$, and then, after initial heating to 80° C., the reaction is initiated by addition of suitable initiators or initiator systems (preferably $Na_2S_2O_8$). The polymer emulsions are subsequently evaporated down (with cyclohexane acting as an azeotrope former for water) and the polymers are thereby isolated.

Process 4:

These polymers are preparable by the solution method in organic solvents (preferably toluene, also, for example, tertiary alcohols). The monomers are introduced in the solvent, the reaction mixture is rendered inert, and then, after initial heating to 70° C., the reaction is initiated by addition of suitable initiators or initiator systems (preferably dilauroyl peroxide). The polymers are isolated by evaporating off the solvent and by subsequent vacuum drying.

Polymers having hydrophobic side chains, uncrosslinked

| No. | Composition | Preparation process |
|---|---|---|
| 1 | 95 g AMPS 5 g Genapol T-080 | 1 |
| 2 | 90 g AMPS 10 g Genapol T-080 | 1 |
| 3 | 85 g AMPS 15 g Genapol T-080 | 1 |
| 4 | 80 g AMPS 20 g Genapol T-080 | 1 |
| 5 | 70 g AMPS 30 g Genapol T-080 | 1 |
| 6 | 50 g AMPS 50 g Genapol T-080 | 3 |
| 7 | 40 g AMPS 60 g Genapol T-080 | 3 |
| 8 | 30 g AMPS 70 g Genapol T-080 | 3 |
| 9 | 20 g AMPS 80 g Genapol T-080 | 3 |
| 10 | 60 g AMPS 60 g BB10 | 4 |
| 11 | 80 g AMPS 20 g BB10 | 4 |
| 12 | 90 g AMPS 10 g BB10 | 3 |
| 13 | 80 g AMPS 20 g BB10 | 1 |
| 14 | 80 g AMPS 20 g Genapol LA040 | 1 |

Polymers having hydrophobic side chains, crosslinked

| No. | Composition | Preparation process |
|---|---|---|
| 15 | 80 g AMPS 20 g Genapol LA040 0.6 g AMA | 1 |
| 16 | 80 g AMPS 20 g Genapol LA040 0.8 g AMA | 1 |
| 17 | 80 g AMPS 20 g Genapol LA040 1.0 g AMA | 1 |
| 18 | 628.73 g AMPS 120.45 g Genapol T-250 6.5 g TMPTA | 2 |
| 19 | 60 g AMPS 40 g BB10 1.9 g TMPTA | 4 |
| 20 | 80 g AMPS 20 g BB10 1.4 g TMPTA | 4 |
| 21 | 90 g AMPS 10 g BB10 1.9 g TMPTA | 4 |
| 22 | 80 g AMPS 20 g BB10 1.9 g TMPTA | 4 |
| 23 | 60 g AMPS 40 g BB10 1.4 g TMPTA | 4 |

Polymers having hydrophobic side chains, crosslinked, grafted

| No. | Composition | Preparation process |
|---|---|---|
| 24 | 95 g AMPS 5 g BB10, 1.9 g TMPTA, 1 g Poly-NVP | 1 |
| 25 | 90 g AMPS 10 g BB10, 1.9 g TMPTA, 1 g Poly-NVP | 1 |
| 26 | 85 g AMPS 15 g BB10, 1.9 g TMPTA, 1 g Poly-NVP | 1 |
| 27 | 90 g AMPS 10 g BB10, 1.9 g TMPTA, 1 g Poly-NVP | 1 |

Polymers having silicon-containing groups, uncrosslinked

| No. | Composition | Preparation process |
|---|---|---|
| 28 | 80 g AMPS, 20 g Silvet 867 | 1 |
| 29 | 80 g AMPS, 50 g Silvet 867 | 4 |

Polymers having silicon-containing groups, crosslinked

| No. | Composition | Preparation process |
|---|---|---|
| 30 | 80 g AMPS, 20 g Silvet 867, 0.5 g MBA | 4 |
| 31 | 80 g AMPS, 20 g Silvet 867, 1.0 g MBA | 1 |
| 32 | 60 g AMPS, 40 g Y-12867, 0.95 g AMA | 1 |
| 33 | 80 g AMPS, 20 g Y-12867, 0.95 g AMA | 1 |
| 34 | 90 g AMPS, 10 g Y-12867, 0.95 g AMA | 1 |
| 35 | 60 g AMPS, 40 g Silvet 7280, 0.95 g AMA | 1 |
| 36 | 80 g AMPS, 20 g Silvet 7280, 0.95 g AMA | 1 |
| 37 | 90 g AMPS, 10 g Silvet 7280, 0.95 g AMA | 1 |
| 38 | 60 g AMPS, 40 g Silvet 7608, 0.95 g AMA | 1 |
| 39 | 80 g AMPS, 20 g Silvet 7608, 0.95 g AMA | 1 |
| 40 | 90 g AMPS, 10 g Silvet 7608, 0.95 g AMA | 1 |

Polymers having hydrophobic side chains and cationic groups, uncrosslinked

| No. | Composition | Preparation process |
|---|---|---|
| 41 | 87.5 g AMPS, 7.5 g Genapol T-110, 5 g DADMAC | 2 |
| 42 | 40 g AMPS, 10 g Genapol T110, 45 g methacrylamide | 2 |
| 43 | 55 g AMPS, 40 g Genapol LA040, 5 g Quat | 1 |
| 44 | 75 g AMPS, 10 g BB10, 6.7 g Quat | 1 |

Polymers having hydrophobic side chains and cationic groups, crosslinked

| No. | Composition | Preparation process |
|---|---|---|
| 45 | 60 g AMPS, 20 g Genapol T-80, 10 g Quat, 10 g HEMA | 1 |
| 46 | 75 g AMPS, 20 g Genapol T-250, 5 g Quat, 1.4 g TMPTA | 1 |
| 47 | 75 g AMPS, 20 g Genapol T-250, 10 g Quat, 1.4 g TMPTA | 1 |
| 48 | 75 g AMPS, 20 g Genapol T-250, 20 g Quat, 1.4 g TMPTA | 1 |

Polymers having fluorine-containing groups

| No. | Composition | Preparation process |
|---|---|---|
| 49 | 94 g AMPS, 2.02 g Fluowet AC 600 | 1 |
| 50 | 80 g AMPS, 20 g perfluorooctylpolyethylene glycol methacrylate, 1 g Span 80 | 3 |

Polymers having fluorine-containing groups, grafted

| No. | Composition | Preparation process |
|---|---|---|
| 51 | 80 g AMPS, 10 g Fluowet AC 600, 5 g Poly-NVP | 1 |
| 52 | 70 g AMPS, 8 g perfluorooctylethyloxyglyceryl methacrylate, 5 g Poly-NVP | 4 |

Polyfunctional polymers

| No. | Composition | Preparation process |
|---|---|---|
| 53 | 80 g AMPS, 10 g Genapol LA070, 10 g Silvet 7608, 1.8 g TMPTA | 1 |
| 54 | 70 g AMPS, 5 g N-vinylpyrrolidone, 15 g Genapol T-250 methacrylate, 10 g Quat, 10 g Poly-NVP | 4 |
| 55 | 80 g AMPS, 5 g N-vinylformamide, 5 g Genapol O-150 methacrylate, 10 g DADMAC, 1.8 g TMPTA, 8 g poly-N-vinylformamide | 2 |

| No. | Composition | Preparation process |
|---|---|---|
| 56 | 70 g AMPS, 5 g N-vinylpyrrolidone, 15 g Genapol T-250 methacrylate, 10 g Quat, 10 g Poly-NVP | 1 |
| 57 | 60 g AMPS, 10 g Genapol-BE-020 methacrylate, 10 g Genapol T-250 acrylate, 20 g Quat, 1 g Span 80 | 1 |
| 58 | 60 g AMPS, 20 g MPEG-750 methacrylate, 10 g methacryloyloxypropyldimethicone, 10 g perfluorooctylpolyethylene glycol methacrylate, 10 g poly[N-vinylcaprolactone-co-acrylic acid] (10/90) | 1 |
| 59 | 80 g AMPS, 5 g N-vinylformamide, 5 g Genapol O-150 methacrylate, 10 g DADMAC, 1.8 g TMPTA | 1 |
| 60 | 70 g AMPS, 10 g Genapol T-250 acrylate, 5 g N-methyl-4-vinylpyridinium chloride, 2.5 g Silvet Y-12867, 2.5 g perfluorohexyl-polyethylene glycol methacrylate, 10 g polyethylene glycol dimethacrylate, 4 g poly[N-vinylcaprolactam] | 1 |
| 61 | 10 g AMPS, 20 g acrylamide, 30 g N-2-vinyl-pyrrolidone, 20 g Silvet 7608, 10 g methacryloyloxypropyldimethicone, 10 g Fluowet AC 812 | 3 |
| 62 | 60 g AMPS, 10 g DADMAC, 10 g Quat, 10 g Genapol-LA-250 crotonate, 10 g methacryloyloxypropyldimethicone, 7 g poly[acrylic acid-co-N-vinylformamide] | 1 |
| 63 | 50 g AMPS, 45 g Silvet 7608, 1.8 g TMPTA, 8 g poly[N-vinylformamide] | 1 |
| 64 | 20 g AMPS, 10 g Genapol T 110, 35 g MAA, 30 g HEMA, 5 g DADMAC | 4 |
| 65 | 20 g AMPS, 80 g BB10, 1.4 g TMPTA | 1 |
| 66 | 75 g AMPS, 20 g BB10, 6.7 g Quat, 1.4 g TMPTA | 1 |
| 67 | 35 g AMPS, 60 g acrylamide, 2 g VIFA, 2.5 g vinylphosphonic acid, 2 mol % Fluowet EA-600 | 4 |

Chemical designation of the reactants:

| | |
|---|---|
| AMPS | acryloyldimethyltaurate, either Na or NH4 salt |
| Genapol ® T-080 | $C_{16}$-$C_{18}$ fatty alcohol polyglycol ether having 8 EO units |
| Genapol ® T-110 | $C_{12}$-$C_{14}$ fatty alcohol polyglycol ether having 11 EO units |
| Genapol ® T-250 | $C_{16}$-$C_{18}$ fatty alcohol polyglycol ether having 25 EO units |
| Genapol ® LA-040 | $C_{12}$-$C_{14}$ fatty alcohol polyglycol ether having 4 EO units |
| Genapol ® LA-070 | $C_{12}$-$C_{14}$ fatty alcohol polyglycol ether having 7 EO units |
| Genapol ® O-150 methacrylate | $C_{16}$-$C_{18}$ fatty alcohol polyglycol ether methacrylate having 15 EO units, |
| Genapol ® LA-250 crotonate | $C_{12}$-$C_{14}$ fatty alcohol polyglycol ether crotonate having 25 EO units |
| Genapol ® T-250 methacrylate | $C_{16}$-$C_{18}$ fatty alcohol polyglycol ether methacrylate having 25 EO units |
| Genapol ® T-250 acrylate | $C_{16}$-$C_{18}$ fatty alcohol polyglycol ether acrylate having 25 EO units |
| BB10 ® | polyoxyethylene(10)behenyl ether |
| TMPTA | trimethylolpropanetriacrylate |
| Poly-NVP | poly-N-vinylpyrrolidone |
| Silvet ® 867 | siloxane-polyalkylene oxide copolymer |
| MBA | methylenebisacrylamide |
| AMA | allyl methacrylate |
| ®Y-12867 | siloxane-polyalkylene oxide copolymer |
| Silvet ® 7608 | polyalkylene oxide-modified heptamethyltrisiloxane |
| Silvet ® 7280 | polyalkylene oxide-modified heptamethyltrisiloxane |
| DADMAC | diallyldimethylammonium chloride |
| HEMA | 2-hydroxyethyl methacrylate |
| Quat | 2-(methacryloyloxy)ethyltrimethyl-ammonium chloride |
| Fluowet ® AC 600 | perfluoroalkylethyl acrylate |
| Span ® 80 | sorbitan ester |

The described grafting of the copolymers with other polymers, which can be carried out optionally, leads to products having a particular polymer morphology and giving rise to optically clear gels in aqueous systems. A potential disadvantage of the copolymers without grafting is a more or less strong opalescence in aqueous solution. The basis for this opalescence is hitherto unavoidable, overcrosslinked polymer fractions which arise in the course of the synthesis and are inadequately swollen in water. This produces light-scattering particles whose size is well above the wavelength of visible light and which are therefore the cause of the opalescence. The described grafting process, which can be carried out optionally, substantially reduces or entirely prevents the formation of overcrosslinked polymer fractions in relation to conventional techniques.

The described incorporation both of cationic charges and of silicon, fluorine or phosphorus atoms into the copolymers, which can be carried out optionally, leads to products which in cosmetic formulations possess particular sensorial and rheological properties. An improvement in the sensorial and rheological properties may be desired in particular in the context of use in rinse-off products (especially hair treatment compositions) or leave-on products (especially O/W emulsions).

The silicon-modified copolymers may partly or fully take over the functions of silicone oils. The use of silicones can be reduced or avoided by means of the copolymers.

In both crosslinked and uncrosslinked form the copolymers exhibit advantageous properties. While crosslinked systems, for example, have exhibited outstanding profiles of properties in respect of emulsion stabilization, it has been possible in particular with the aid of the uncrosslinked versions to thicken surfactant-containing solutions. The same is true of electrolyte-containing systems, which are known to be very difficult if not impossible to thicken with polyelectrolytes.

The copolymers have diverse possibilities for use and are suitable, for example, for use in aqueous-alcoholic and aqueous surfactant formulations, emulsions, suspensions, dispersions, and powders.

The copolymers can be used as thickeners for compositions on an aqueous or aqueous-alcoholic basis, examples being hair gels. The copolymers are additionally suitable as stabilizers, dispersants, and bodying agents for aqueous surfactant preparations, examples being shampoos, shower baths, shower gels, foam baths, and the like.

The thickening action of the copolymers in aqueous surfactant compositions is boosted by an association between the polymer side chains and the surfactants, and can be controlled through the choice of the side chains of the copolymers and through the choice of the surfactants.

The suspending or dispersing and stabilizing action of the copolymers in aqueous surfactant compositions is due to the association of the polymer side chains and/or functional groups in main chain and side chain with the liquid components that are insoluble in aqueous surfactant compositions, examples being silicone oils, and/or the insoluble components, an example being zinc pyrithione.

The copolymers are likewise suitable as thickeners and dispersants, as emulsifiers, suspension media with thickening effect, and bodying agents for emulsions and suspensions, and also as lubricants, tackifiers, thickeners, dispersants and emulsifiers of decorative preparations containing solids. In this context it is also possible to use mixtures of the copolymers. The emulsifying, stabilizing and/or bodying action of the copolymers in emulsions is due to and/or boosted by an association of the polymer side chains with one another, and also by an interaction of the polymer side chains with the hydrophobic oil components.

The emulsions can be alternatively water-in-oil emulsions or oil-in-water emulsions, microemulsions or multiple emulsions. The emulsions can be prepared conventionally, i.e., for example, by hot, hot/cold or PIT emulsification.

The nonaqueous fraction of the emulsions, composed largely of the emulsifier, the thickener, and the oily substance, is normally from 5 to 95% by weight, preferably from 15 to 75% by weight. It follows from this that the emulsions can contain from 5 to 95% by weight, preferably from 25 to 85% by weight, of water, irrespective of whether lotions with a comparatively low viscosity or creams and ointments with high viscosity are to be prepared.

In one preferred embodiment the copolymers are used in rinse-off products, preferably shampoos, body washes, shower gels, and foam baths.

In another embodiment the copolymers are used in leave-on products, preferably skincare compositions, day creams, night creams, beauty creams, nutrient creams, body lotions, ointments, sun protection compositions, lipcare compositions, and deodorants.

They are also suitable, furthermore, for surfactant-free aqueous compositions and emulsions, for example, for hair treatments and hair rinses, and hair gels, and also permanent waving compositions, hair-coloring compositions, and for decorative cosmetics, examples being makeup, eye shadows, lipsticks, mascara, and the like.

The compositions of the invention contain, based on the finished compositions, preferably from 0.01 to 10% by weight, more preferably from 0.1 to 5% by weight, very preferably from 0.5 to 3% by weight, of copolymers.

The compositions of the invention may comprise anionic, cationic, nonionic, zwitterionic and/or amphoteric surfactants.

The total amount of the surfactants used in the compositions of the invention (e.g., in the case of rinse-off products), based on the finished compositions, is preferably from 2 to 70% by weight, more preferably between 5 and 40% by weight, very preferably from 12 and 35% by weight.

Preferred anionic surfactants are ($C_{10}$-$C_{20}$)-alkyl and alkylene carboxylates, alkyl ether carboxylates, fatty alcohol sulfates, fatty alcohol ether sulfates, alkylamide sulfates and sulfonates, fatty acid alkylamide polyglycol ether sulfates, alkanesulfonates and hydroxyalkanesulfonates, olefinsulfonates, acyl esters of isethionates, α-sulfo fatty acid esters, alkylbenzenesulfonates, alkylphenol glycol ether sulfonates, sulfosuccinates, sulfosuccinic monoesters and diesters, fatty alcohol ether phosphates, protein/fatty acid condensation products, alkyl monoglyceride sulfates and sulfonates, alkylglyceride ether sulfonates, fatty acid methyltaurides, fatty acid sarcosinates, sulforicinoleates, and acylglutamates. These compounds and their mixtures are used in the form of their water-soluble or water-dispersible salts, examples being the sodium, potassium, magnesium, ammonium, mono-, di-, and triethanolammonium, and analogous alkylammonium salts.

The weight fraction of the anionic surfactants, based on the finished compositions, is preferably from 2 to 30% by weight, more preferably from 5 to 25% by weight, very preferably from 12 to 22% by weight.

Preferred cationic surfactants are quaternary ammonium salts such as di-($C_{10}$-$C_{24}$)-alkyl-dimethylammonium chloride or bromide, preferably di-($C_{12}$-$C_{18}$)-alkyl-dimethylammonium chloride or bromide; ($C_{10}$-$C_{24}$)-alkyl-dimethylethylammonium chloride or bromide; ($C_{10}$-$C_{24}$)-alkyl-trimethylammonium chloride or bromide, preferably cetyltrimethylammonium chloride or bromide and ($C_{20}$-$C_{22}$)-alkyl-trimethylammonium chloride or bromide; ($C_{10}$-$C_{24}$)-alkyl-dimethylbenzylammonium chloride or bromide, preferably ($C_{12}$-$C_{18}$)-alkyl-dimethylbenzylammonium chloride; N-($C_{10}$-$C_{18}$)-alkyl-pyridinium chloride or bromide, preferably N-($C_{12}$-$C_{16}$)-alkyl-pyridinium chloride or bromide; N-($C_{10}$-$C_{16}$)-alkyl-isoquinolinium chloride, bromide or monoalkyl sulfate; N-($C_{12}$-$C_{18}$)-alkyl-polyoylaminoformylmethylpyridinium chloride; N-($C_{12}$-$C_{18}$)-alkyl-N-methylmorpholinium chloride, bromide or monoalkyl sulfate; N-($C_{12}$-$C_{18}$)-alkyl-N-ethylmorpholinium chloride, bromide or monoalkyl sulfate; ($C_{16}$-$C_{18}$)-alkyl-pentaoxethylammonium chloride; diisobutylphenoxyethoxyethyldimethylbenzylammonium chloride; salts of N,N-diethylaminoethylstearylamide and -oleylamide with hydrochloric acid, acetic acid, lactic acid, citric acid, phosphoric acid; N-acylaminoethyl-N,N-diethyl-N-methylammonium chloride, bromide or monoalkyl sulfate, and N-acylaminoethyl- N,N-diethyl-N-benzylammonium chloride, bromide or monoalkyl sulfate, acyl standing preferably for stearyl or oleyl.

The weight fraction of the cationic surfactants is preferably from 1 to 10% by weight, more preferably from 2 to 7% by weight, very preferably from 3 to 5% by weight.

Preferred nonionic surfactants include fatty alcohol ethoxylates (alkylpolyethylene glycols); alkylphenol polyethylene glycols; alkylmercaptan polyethylene glycols; fatty amine ethoxylates (alkylaminopolyethylene glycols); fatty acid ethoxylates (acylpolyethylene glycols); polypropylene glycol ethoxylates (Pluronics®); fatty acid alkylol amides, (fatty acid amide polyethylene glycols); N-alkyl-, N-alkoxypolyhydroxy-fatty acid amide, sucrose esters; sorbitol esters and polyglycol ethers. The weight fraction of the nonionic surfactants in the compositions of the invention (e.g., in the case of rinse-off products) is preferably in the range from 1 to 20% by weight, more preferably from 2 to 10%, very preferably from 3 to 7% by weight.

Preferred amphosurfactants are $N-(C_{12}-C_{18})$-alkyl-β-aminopropionates and $N-(C_{12}-C_{18})$-alkyl-β-iminodipropionates as alkali metal salts and mono-, di-, and trialkylammonium salts; N-acylaminoalkyl-N,N-dimethylacetobetaine, preferably $N-(C_8-C_{18})$-acylaminopropyl-N,N-dimethylacetobetaine; $(C_{12}-C_{18})$-alkyl-dimethylsulfopropylbetaine; amphosurfactants based on imidazoline (trade name: Miranol®, Steinapon®), preferably the sodium salt of 1-(β-carboxymethyloxyethyl)-1-(carboxymethyl)-2-laurylimidazolinium; amine oxide, e.g., $(C_{12}-C_{18})$-alkyl-dimethylamine oxide, fatty acid amidoalkyldimethylamine oxide.

The weight fraction of the amphoteric surfactants is preferably from 0.5 to 20% by weight, more preferably from 1 to 10% by weight.

Preferred surfactants are lauryl sulfate, laureth sulfate, cocoamidopropylbetaine, sodium cocoylglutamate, and lauroamphoacetate.

In one preferred embodiment the compositions further comprise as foam-boosting agents cosurfactants from the group consisting of alkylbetaines, alkylamidobetaines, aminopropionates, aminoglycinates, imidazolinium betaines and sulfobetaines, amine oxides, fatty acid alkanol amides, and polyhydroxyamides.

As further auxiliaries and additives the compositions of the invention may comprise oily substances, emulsifiers and coemulsifiers, and also other additions customary in cosmetology, such as cationic polymers, film formers, superfatting agents, stabilizers, active biogenic substances, glycerol, preservatives, pearlizing agents, dyes and fragrances, solvents, opacifiers, and also protein derivatives such as gelatin, collagen hydrolysates, natural or synthetic-based polypeptides, egg yolk, lecithin, lanolin and lanolin derivatives, fatty alcohols, silicones, deodorants, substances with a keratolytic and keratoplastic action, enzymes, and carrier substances. The compositions of the invention may also have antimicrobial agents added to them.

An oily substance is any fatty substance which is liquid at room temperature (25° C.).

The fatty phase may comprise one or more oils selected preferably from the following oils:
  silicone oils, volatile or nonvolatile, linear, branched or cyclic, optionally with organic modification; phenylsilicones; silicone resins and silicone gums, solid or liquid at room temperature; mineral oils, such as paraffin oil or vaseline oil; oils of animal origin, such as perhydrosqualene or lanolin; oils of plant origin, such as liquid triglycerides, e.g., sunflower oil, corn oil, soybean oil, rice oil, jojoba oil, babusscu oil, pumpkin oil, grapeseed oil, sesame oil, walnut oil, apricot oil, macadamia oil, avocado oil, sweet almond oil, lady's-smock oil, castor oil, triglycerides of caprylic/capric acids, olive oil, peanut oil, rapeseed oil, and coconut oil;
  synthetic oils, such as purcellin oil, isoparaffins, linear and/or branched fatty alcohols and fatty acid esters, preferably guerbet alcohols having 6 to 18, preferably 8 to 10, carbon atoms; esters of linear $(C_6-C_{13})$ fatty acids with linear $(C_6-C_{20})$ fatty alcohols; esters of branched $(C_6-C_{13})$ carboxylic acids with linear $(C_6-C_{20})$ fatty alcohols, esters of linear $(C_6-C_{18})$ fatty acids with branched alcohols, especially 2-ethylhexanol; esters of linear and/or branched fatty acids with polyhydric alcohols (such as dimerdiol or trimerdiol, for example) and/or guerbet alcohols; triglycerides based on $(C_6-C_{10})$ fatty acids; esters, such as dioctyl adipate, diisopropyl dimer dilinoleate; propylene glycols/dicaprylate or waxes such as beeswax, paraffin wax or microwaxes, alone or in combination with hydrophilic waxes, such as cetylstearyl alcohol, for example; fluorinated and perfluorinated oils; fluorinated silicone oils; mixtures of the aforementioned substances.

Suitable nonionogenic coemulsifiers include adducts of from 0 to 30 mol of ethylene oxide and/or from 0 to 5 mol of propylene oxide with linear fatty alcohols having 8 to 22 carbon atoms, with fatty acids having 12 to 22 carbon atoms, with alkylphenols having 8 to 15 carbon atoms in the alkyl group, and with sorbitan or sorbitol esters; $(C_{12}-C_{18})$ fatty acid monoesters and diesters of adducts of from 0 to 30 mol of ethylene oxide with glycerol; glycerol monoesters and diesters and sorbitan monoesters and diesters of saturated and unsaturated fatty acids having 6 to 22 carbon atoms and, where appropriate, their ethylene oxide adducts; adducts of from 15 to 60 mol of ethylene oxide with castor oil and/or hydrogenated castor oil; polyol esters and especially polyglycerol esters, such as polyglyceryl polyricinoleate and polyglyceryl poly-12-hydroxystearate, for example. Likewise suitable are mixtures of compounds from one or more of these classes of substance.

Examples of suitable ionogenic coemulsifiers include anionic emulsifiers, such as mono -, di- or tri-phosphoric esters, but also cationic emulsifiers such as mono-, di-, and tri-alkyl quats and their polymeric derivatives.

Suitable cationic polymers include those known under the INCI designation "Polyquaternium", especially Polyquaternium-31, Polyquaternium-16, Polyquaternium-24, Polyquaternium-7, Polyquaternium-22, Polyquaternium-39, Polyquaternium-28, Polyquaternium-2, Polyquaternium-10, Polyquaternium-11, and also Polyquaternium 37&mineral oil&PPG tridecith (Salcare SC95), PVP-dimethylaminoethyl methacrylate copolymer, guar-hydroxypropyltriammonium chlorides, and also calcium alginate and ammonium alginate. It is additionally possible to employ cationic cellulose derivatives; cationic starch; copolymers of diallylammonium salts and acrylamides; quaternized vinylpyrrolidone/vinylimidazole polymers; condensation products of polyglycols and amines; quaternized collagen polypeptides; quaternized wheat polypeptides; polyethyleneimines; cationic silicone polymers, such as amidomethicones, for example; copolymers of adipic acid and dimethylaminohydroxypropyldiethylenetriamine; polyaminopolyamide and cationic chitin derivatives, such as chitosan, for example.

Examples of suitable silicone compounds are dimethylpolysiloxane, methylphenylpolysiloxanes, cyclic silicones, and amino-, fatty acid-, alcohol-, polyether-, epoxy-, fluoro- and/or alkyl-modified silicone compounds, and also polyalkylsiloxanes, polyalkylarylsiloxanes, polyethersiloxanes, as described in U.S. Pat. No. 5,104,645 and the documents cited therein, which at room temperature may be present either in liquid form or in resin form.

Suitable film formers, depending on the intended application, are water-soluble polyurethanes, for example, C10-polycarbamyl polyglyceryl esters, polyvinyl alcohol, polyvinylpyrrolidone, copolymers thereof, for example vinylpyrrolidone/vinyl acetate copolymer, water-soluble acrylic acid polymers/copolymers and their esters or salts, examples being partial ester copolymers of acrylic/methacrylic acid and polyethylene glycol ethers of fatty alcohols, such as acrylate/steareth-20 methacrylate copolymer, water-soluble cellulose, examples being hydroxymethylcellulose, hydroxyethylcellulose, hydroxypropylcellulose, water-soluble quaterniums, polyquaterniums, carboxyvinyl polymers, such as carbomers and their salts, polysaccharides, polydextrose for example, and glucan.

As superfatting agents it is possible to use substances such as, for example, polyethoxylated lanolin derivatives, lecithin derivatives, polyol fatty acid esters, monoglycerides, and fatty acid alkanol amides, the latter serving simultaneously as foam stabilizers. Moisturizers available include for example isopropyl palmitate, glycerol and/or sorbitol.

As stabilizers it is possible to use metal salts of fatty acids, such as magnesium, aluminum and/or zinc stearate, for example.

Active biogenic substances are to be understood as including, for example, plant extracts and vitamin complexes.

Additionally, the formulations of the invention may comprise organic solvents. Suitable organic solvents include in principle all monohydric or polyhydric alcohols. Preference is given to using alcohols having 1 to 4 carbon atoms such as ethanol, propanol, isopropanol, n-butanol, isobutanol, t-butanol, glycerol, and mixtures of said alcohols. Further preferred alcohols are polyethylene glycols having a relative molecular mass of less than 2 000. Particular preference is given to the use of polyethylene glycol having a relative molecular mass of between 200 and 600 in amounts of up to 45% by weight and of polyethylene glycol having a relative molecular mass of between 400 and 600 in amounts of from 5 to 25% by weight. Further suitable solvents are, for example, triacetin (glyceryl triacetate) and 1-methoxy-2-propanol.

The compositions of the invention can be blended with conventional ceramides, pseudoceramides, fatty acid N-alkylpolyhydroxyalkyl amides, cholesterol, cholesterol fatty acid esters, fatty acids, triglycerides, cerebrosides, phospholipids, and similar substances as a care additive.

Examples of suitable UV filters include 4-aminobenzoic acid; 3-(4'-trimethylammonium)benzylideneboran-2-one methylsulfate; 3,3,5-trimethylcyclohexyl salicylate; 2-hydroxy-4-methoxybenzophenone; 2-phenylbenzimidazole-5-sulfonic acid and its potassium, sodium, and triethanolamine salts; 3,3'-(1,4-phenylenedimethine)bis(7,7-dimethyl-2-oxobicyclo[2.2.1]heptane-1-methanesulfonic acid and its salts; 1-(4-tert-butylphenyl)-3-(4-methoxyphenyl)propane-1,3-dione, 3-(4'-sulfo)-benzylidenebornan-2-one and its salts; 2-ethylhexyl 2-cyano-3,3-diphenylacrylate; polymer of N-[2 (and 4)-(2-oxoborn-3-ylidenemethyl)benzyl]acrylamide; 2-ethylhexyl 4-methoxycinnamate; ethoxylated ethyl 4-aminobenzoate; isoamyl 4-methoxycinnamate; 2,4,6-tris[p-(2-ethylhexyloxycarbonyl)anilino]-1,3,5-triazine; 2-(2H-benzotriazol-2-yl)-4-methyl-6-(2-methyl-3-(1,3,3,3-tetramethyl-1-(trimethylsilyloxy)disiloxanyl)propyl)phenol; 4,4'-[(6-[4-((1,1-dimethylethyl)aminocarbonyl)phenylamino]-1,3,5-triazin-2,4-yl)diimino]bis(benzoic acid 2-ethylhexyl ester); 3-(4'-methylbenzylidene)-D,L-camphor; 3-benzylidene camphor; 2-ethylhexyl salicylate; 2-ethylhexyl 4-dimethylaminobenzoate; hydroxy-4-methoxybenzophenone-5-sulfonic acid (sulisobenzone) and the sodium salt; and/or 4-isopropylbenzyl salicylate.

As pigments/micropigments it is possible, for example, to use microfine titanium dioxide, mica-titanium oxide, iron oxides, mica-iron oxide, zinc oxide, silicon oxides, ultramarine blue, and chromium oxides.

Examples of suitable antioxidants include superoxide dismutase, tocopherol (vitamin E) and ascorbic acid (vitamin C).

Examples of suitable preservatives include phenoxyethanol, parabens, pentanediol or sorbic acid.

As dyes it is possible to use the substances which are suitable and approved for cosmetic purposes.

Suitable active antifungal substances (fungicides) include preferably ketoconazole, oxiconazole, bifonazole, butoconazole, cloconazole, clotrimazole, econazole, enilconazole, fenticonazole, isoconazole, miconazole, sulconazole, tioconazole, fluconazole, itraconazole, terconazole, naftifine and terbinafine, Zn pyrithione, and octopirox.

In order to adjust the rheological properties of aqueous or solvent-containing emulsions or suspensions the technical literature specifies a multiplicity of different systems. Those known include, for example, cellulose ethers and other cellulose derivatives (e.g., carboxymethylcellulose, hydroxyethylcellulose), gelatin, starch and starch derivatives, sodium alginates, fatty acid polyethylene glycol esters, agar agar, tragacanth or dextrins. Synthetic polymers employed include a variety of materials, such as polyvinyl alcohols, polyacrylamides, polyvinylamides, polysulfonic acids, polyacrylic acid, polyacrylates, polyvinylpyrrolidone, polyvinyl methyl ethers, polyethylene oxides, copolymers of maleic anhydride and vinyl methyl ether, and also various mixtures and copolymers of the aforementioned compounds, including their various salts and esters. These polymers may alternatively be crosslinked or noncrosslinked.

Essential for the invention is that the acryloyldimethyltaurine copolymers described can be employed even without the use of an additional coemulsifier and/or without the use of an additional bodying agent. The use of coemulsifiers and/or bodying agents is therefore not mandatory, but is possible. Combination with other known coemulsifiers and/or bodying agents may be desirable for establishing specific cosmetic profiles and for utilizing synergistic effects.

The compositions of the invention are normally adjusted to a pH in the range from 2 to 12, preferably from 3 to 8.

The nature of the compositions of the invention is extremely advantageous: the emulsions are creamy and ointmentlike and above all do not have the gel-like or even gelatin-like appearance of certain prior art emulsions in which the external aqueous phase is thickened.

The cosmetic feel on the skin is also very good: on application, the emulsion imparts a sensation of freshness and of comfort, and at the same time has a rich and nourishing effect; it is soft and luxurious and in no way sticky.

The examples and applications below are intended to illustrate the invention, though without restricting it thereto (all percentages are by weight). The copolymers used in the examples are representatives of the particularly preferred copolymers 1 to 67 already listed in the description. They were prepared by the indicated processes 1, 2, 3 or 4 using the preferred initiators and solvents.

EXAMPLE 1

O/W Skin Milk

Composition

| | | |
|---|---|---|
| A | Copolymer No. 21 | 0.50% |
| | Isopropyl palmitate | 4.00% |
| | Almond oil 5.00% | 4.00% |
| | Wheatgerm oil | 1.00% |
| | ®Cetiol SN (Henkel) | 8.00% |
| | Cetearyl isononanoate | |
| B | ®Aristoflex AVC (Clariant) | 0.30% |
| | Ammonium acryloyldimethyltaurate-VP copolymer | |
| C | Water | ad 100% |
| D | Fragrances | 0.30% |

Preparation

| | |
|---|---|
| I | Mix A and B, then add C. |
| II | Stir D into I. |
| III | Homogenize emulsion. |

EXAMPLE 2

O/W Aftersun Milk

Composition:

| | | |
|---|---|---|
| A | Copolymer No. 34 | 1.00% |
| | Isopropyl palmitate | 5.00% |
| | ®Cetiol SN (Henkel) | 4.00% |
| | Cetearyl isononanoate | |
| | Soybean oil | 4.00% |
| | ®Miglyol 812 (Dynamit Nobel) | 3.00% |
| | Caprylic/capric triglycerides | |
| | Jojoba oil | 3.00% |
| | Wheatgerm oil | 1.00% |
| D | ®AQUAMOLLIN BC powder, high-conc. (Clariant) | 0.10% |
| | Ethylenediamine tetraacetic acid sodium salt | |
| | Citric acid (10% strength) | 0.30% |
| | Water | 68.80% |
| | Glycerol | 3.00% |
| | ALLANTOIN (Clariant) | 0.20% |
| | Allantoin | |
| | Preservative | q.s. |
| E | Ethanol | 1.50% |
| | Perfume oil | 0.30% |

Preparation

| | |
|---|---|
| I | Stir together the components of A homogeneously. |
| II | At about 35° C. stir D into I. |
| III | Homogenize the emulsion. |

EXAMPLE 3

W/O Cream

Composition

| | | |
|---|---|---|
| A | ®HOSTACERIN DGI (Clariant) | 4.00% |
| | Polyglyceryl-2 sesquiisostearate | |
| | Beeswax | 2.00% |
| | Copolymer No. 10 | 1.5% |
| | Mineral oil, low viscosity | 5.00% |
| | Vaseline | 10.00% |
| | ®Cetiol V (Henkel KGaA) | 5.00% |
| | Decyl oleate | |
| B | 1,2-Propylene glycol | 3.00% |
| | Water | 69.10% |
| | Preservative | q.s. |
| C | Fragrance | 0.40% |

Preparation

| | |
|---|---|
| I | Melt A at 80° C. |
| II | Heat B to 80° C. |
| III | Stir II into I. |
| IV | Stir until cool. |
| V | At 35° C. add C to IV. |

EXAMPLES OF SURFACTANT FORMULATIONS

EXAMPLE 4

Body Wash

Composition

| | | |
|---|---|---|
| A | ®GENAPOL LRO liquid (Clariant) | 40.00% |
| | Sodium laureth sulfate | |
| B | Fragrance | 0.30% |
| C | Water | 52.70% |
| | Dye | q.s. |
| | Preservative | q.s. |
| | ®GENAGEN LDA (Clariant) | 6.00% |
| | Disodium lauroamphodiacetate | |
| | Citric acid | q.s. |
| D | Copolymer No. 44 | 1.00% |

Preparation

| | |
|---|---|
| I | Stir B into A. |
| II | Add components from C successively to I. |
| III | Adjust pH to 5.5. |
| IV | Adjust the viscosity by stirring D into II. |

EXAMPLE 5

Baby Shampoo

Composition

| | | | |
|---|---|---|---|
| A | Water | | 60.70% |
| | ® GENAPOL ZRO liquid (Clariant) | | 25.00% |
| | Sodium laureth sulfate | | |
| | ® HOSTAPON CLG (Clariant) | | 8.00% |
| | Sodium lauroyl glutamate | | |
| | ® GENAPOL SBE (Clariant) | | 5.00% |
| | Disodium laureth sulfosuccinate | | |
| | Fragrance | | 0.30% |
| | Dye solution | | q.s. |
| | Preservative | | q.s. |
| B | Copolymer No. 44 | | 1.00% |

Preparation

| | |
|---|---|
| I | Dissolve B in A. |
| II | Adjust pH if appropriate. |

EXAMPLE 6

Antidandruff Shampoo, Clear

Composition

| | | |
|---|---|---|
| A | ® OCTOPIROX (Clariant) | 0.50% |
| | Piroctone olamine | |
| B | Water | 10.00% |
| C | ® GENAPOL LRO LIQUID (Clariant) | 30.00% |
| | Sodium laureth sulfate | |
| D | ® Belsil DMC 6032 (Wacker Chemie) | 1.50% |
| | Dimethicone copolyol acetate | |
| | Fragrance | 0.30% |
| E | ® ALLANTOIN (Clariant) | 0.30% |
| F | Water | 46.40% |
| G | Dye solution | q.s. |
| | Panthenol (Hoffmann La Roche) | 1.00% |
| | ® GENAGEN CAB (Clariant) | 8.00% |
| | Cocamidopropylbetaine | |
| H | Copolymer No. 28 | 1.10% |

Preparation

| | |
|---|---|
| I | Mix A with B. |
| II | Stir C into I until clear solution is obtained. |
| III | Add components from D successively to I. |
| IV | Stir E into F with heating and then stir mixture into I. |
| V | Add components from G successively to I. |
| VI | Adjust pH if appropriate. |
| VII | Adjust the viscosity by stirring H into I. |

EXAMPLE 7

Antidandruff Shampoo, Pearlescent

Composition

| | | |
|---|---|---|
| A | Water | 38.7% |
| B | ® HOSTAPON SCI-65 (Clariant) | 3.00% |
| | Sodium cocoyl isethionate | |
| C | ® GENAPOL LRO liquid (Clariant) | 35.00% |
| | Sodium laureth sulfate | |
| | ® HOSTAPON KCG (Clariant) | 5.00% |
| | Sodium cocoyl glucamate | |
| | ® Belsil DMC 6032 (Wacker) | 1.00% |
| | Dimethicone copolyol acetate | |
| | Fragrance | 0.30% |
| | ® GENAGEN CAB (Clariant) | 9.00% |
| | ® Cocamidopropylbetaine | |
| | GENAPOL TSM (Clariant) | 4.00% |
| | PEG-3 distearate (and) sodium laureth sulfate | |
| | Merquat 550 | 0.50% |
| | Polyquaternium-7 | |
| | Zinc omadine FPS (Olin) | |
| | Zinc pyrithione (48%) | 2.50% |
| | Copolymer No. 14 | 1.00% |
| | Dye solution | q.s. |
| | Preservative | q.s. |

Preparation

| | |
|---|---|
| I | Dissolve B in A at 80° C. |
| II | After cooling to about 35° C., add components C successively. |

EXAMPLES OF GELS

EXAMPLE 8

Hair Gel with Conditioning Properties

Composition

| | | |
|---|---|---|
| A | Water | 92.00% |
| | Panthenol | 1.50% |
| | UVAsorb S5 | 0.05% |
| | Benzophenone-4 | |
| | Dye solution | q.s. |
| | Preservative | q.s. |
| B | ® Emulsogen HCO 040 (Clariant) | 0.50% |
| | PEG-40 hydrogenated castor oil | |
| | Perfume | q.s. |
| C | Copolymer No. 26 | 2.00% |
| D | Gafquat 755N (ISP) | 2.50% |
| | Polyquaternium-11 | |

Preparation

| | |
|---|---|
| I | Mix components A. |
| II | Mix components B and add to I. |
| III | Add C to D to I. |

EXAMPLE 9

Hair Gel with Strong Hold

Composition

| | | |
|---|---|---|
| A | Water | 91.50% |
| | PVP K-30 (ISP) | 4.00 |
| | PVP | |
| | Panthenol | 0.50% |
| | UVAsorb S5 | 0.05% |
| | Benzophenone-4 | |
| | Dye solution | q.s. |
| | Preservative | q.s. |
| B | Abil B 8851 (Goldschmidt) | 1.00% |
| | Dimethicone copolyol | |
| | ® Emulsogen HCO 040 (Clariant) | 0.50% |
| | PEG-40 hydrogenated castor oil | |
| | Perfume | q.s. |
| C | Copolymer No. 63 | 2.50% |

Preparation

| | |
|---|---|
| I | Mix components A. |
| II | Add components B to I. |
| III | Add components C to I. |

What is claimed is:

1. A cosmetic, dermatological or pharmaceutical composition in the form of a surfactant composition or an emulsion having a nonaqueous fraction which comprises a surfactant, an oily substance, and at least one copolymer obtained by free-radical copolymerization of
   A) acryloyldimethyltaurine and/or acryloyldimethyltaurates,
   B) optionally, one or more further olefinically unsaturated, noncationic, comonomer which have at least one oxygen, nitrogen, sulfur or phosphorus atom and possess a molecular weight of less than 500 g/mol,
   C) optionally, one or more olefinically unsaturated, cationic comonomer which has at least one oxygen, nitrogen, sulfur or phosphorus atom and has a molecular weight of less than 500 g/mol,
   D) one or more silicon-containing component capable of free-radical polymerization and having a functionality of at least one, at least one silicon-containing component being a compound selected from the group consisting of

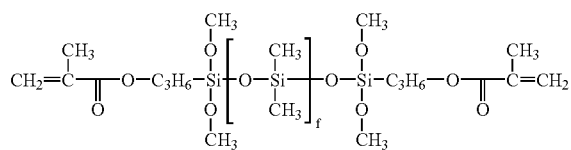

in which f=2 to 500,

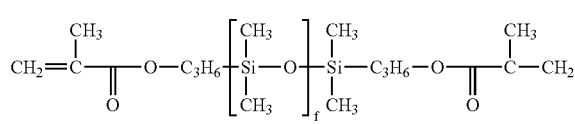

in which f=2 to 500,

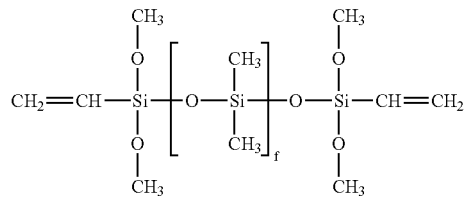

in which f=2-500, and mixtures thereof,
   E) optionally, one or more fluorine-containing component capable of free-radical polymerization and having a functionality of at least one,
   F) optionally, one or more olefinically mono- or polyunsaturated, macromonomer each possessing at least one oxygen, nitrogen, sulfur or phosphorus atom and having a number-average molecular weight of greater than or equal to 200 g/mol, the macromonomer not being silicon-containing component D) or fluorine-containing component E),
   G) optionally, the copolymerization taking place in the presence of at least one polymeric additive having number-average molecular weights of from 200 g/mol to $10^9$ g/mol
   wherein the nonaqueous fraction comprises from 5 to 95 wt-% of said cosmetic, dermatological or pharmaceutical composition.

2. The composition as claimed in claim 1, wherein the comonomer B) is selected from the group consisting of unsaturated carboxylic acids, salts of unsaturated carboxylic acids, anhydrides of unsaturated carboxylic acids, esters of unsaturated carboxylic acids with aliphatic, olefinic, cycloaliphatic, arylaliphatic or aromatic alcohols having 1 to 22 carbon atoms, open-chain N-vinyl amides, cyclic N-vinyl amides having a ring size of from 3 to 9, amides of acrylic acid, amides of methacrylic acid, amides of substituted acrylic acids, amides of substituted methacrylic acids, 2-vinylpyridine, 4-vinylpyridine, vinyl acetate; styrene, acrylonitrile, vinyl chloride, vinylidene chloride, tetrafluoroethylene. vinylphosphonic acid or the esters or salts thereof, vinylsulfonic acid or the esters or salts thereof, allylphosphonic acid or the esters or salts thereof, methallylsultonic acid or the esters or salts thereof, and mixtures thereof.

3. The composition of claim 1 wherein the comonomer C) is selected from the group consisting of
   diallyldimethylammonium chloride (DADMAC),
   [2-(methacryloyloxy)ethyl]trimethylammonium chloride (MAPTAC),
   [2-(acryloyloxy)ethyl]trimethylammonium chloride,
   [2-methacrylamidoethyl]trimethylammonium chloride,
   [2-(acrylamido)ethyl]trimethylammonium chloride,
   N-methyl-2-vinylpyridinium chloride,
   N-methyl-4-vinylpyridinium chloride,
   dimethylaminoethyl methacrylate,
   dimethylamlnopropyimethacrylamide,
   methacryloylethyl N-oxide,
   methacryloylethylbetaine, and mixtures thereof.

4. The composition of claim 1, wherein the fluorine-containing component E) is a compound of the formula (II)

$$R^1-Y-C_rH_2{}_rC_sF_2{}_sCF_3 \qquad (II)$$

where
R¹ is a polymerizable function of a vinylically unsaturated compound;
Y is a chemical bridge, and
r, s are stoichiometric coefficients which independently of one another are numbers between 0 and 200.

5. The composition of claim 1, wherein the macromonomer F) is a compound of the formula (III)

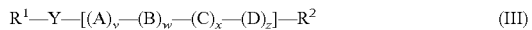

$R^1-Y-[(A)_v-(B)_w-(C)_x-(D)_z]-R^2$ (III)

where R¹ is a polymerizable function of a vinylically unsaturated compound;
Y is a bridging group;
A, B, C, and D independently of one another are discrete chemical repeating units;
v, w, x, and z independently of one another amount to from 0 to 500, the sum of v, w, x, and z being on average $\geq 1$; and
R² is a linear or branched aliphatic, olefinic, cycloaliphatic, arylaliphatic or aromatic
($C_1$-$C_{50}$) hydrocarbon radical, OH, —$NH_2$ or —$N(CH_3)_2$ or is [—Y—R¹].

6. The composition of claim 1, wherein the polymeric additive G) is selected from the group consisting of polyalkylene glycol, alkylpolyglycol, and mixtures thereof or a homopolymer or copolymer of a compound selected from the group consisting of N-vinylformamide, N-vinylacetamide, N-vinylpyrrolidone, ethylene oxide, propylene oxide, acryloyldimethyltaurine, N-vinylcaprolactam, N-vinylmethylacetamide, acrylamide, acrylic acid, methacrylic acid, N-vinylmorpholide, hydroxymethyl methacrylate, diallyldimethylammonium chloride (DADMAC), [2-(methacryloyloxy)ethyl]trimethylammonium chloride (MAPTAC), and mixtures thereof.

7. The composition of claim 1, wherein the copolymerization takes place in the presence of at least one polymeric additive G).

8. The composition of claim 1, wherein the copolymer is crosslinked.

9. The composition of claim 1, wherein the copolymer is prepared by precipitation polymerization in tert-butanol.

10. The composition of claim 1, which comprises, based on a finished composition, from 0.01 to 10% by weight of the copolymer.

11. The composition of claim 1, wherein the copolymer is water-soluble or water-swellable.

12. The composition of claim 5, wherein, R¹ is a radical selected from the group consisting of vinyl, allyl, methallyl, methylvinyl, acryloyl, methacryloyl, crotonyl, senecionyl, itaconyl, maleyl, fumaryl, styryl, and mixtures thereof.

13. The composition of claim 5, wherein the bridging group Y is selected from the group consisting of —O—, —S—, —C—(O)—, —O—, —O—$CH_2$—CH(O—)—$CH_2OH$, —O—$CH_2$—CH(OH)—$CH_2O$—, —O—$SO_2$—O—, —SO—O—, —PH—, —P($CH_3$)—, —$PO_3$—, —NH—, —N($CH_3$)—, and mixtures thereof.

14. The composition of claim 5, wherein the discrete repeating units of A, B, C, and D are originating from a unit selected from the group consisting of acrylamide, methacrylamide, ethylene oxide, propylene oxide, AMPS, acrylic acid, methacrylic acid, methyl methacrylate, acrylonitrile, maleic acid, vinyl acetate, styrene, 1,3-butadiene, isoprene, isobutene, diethylacrylamide, and diisopropylacryiamide.

15. The composition of claim 5, wherein the discrete repeating units of A, B, C, and D are originating from a unit of ethylene oxide or propylene oxide.

16. The composition of claim 5, wherein v, w, x, and z independently of one another amount to from 1 to 30.

17. The composition of claim 4 wherein, R¹ is a radical selected from the group consisting of vinyl, allyl, methallyl, methylvinyl, acryloyl, methacryloyl, crotonyl, senecionyl, itaconyl, maleyl, fumaryl, styryl, and mixtures thereof.

18. The composition of claim 4, wherein the chemical bridge Y is selected from the group consisting of —O—; —C(O)—; —C(O)—O—; —S—; —O—$CH_2$—CH(O—)—$CH_2OH$ ; —O—$CH_2$—CH(OH)—$CH_2$—O—; —O—S(O)—O—; —PH—; —P($CH_3$)—; —$PO_3$—; —NH—; —N($CH_3$)—; —O—($C_1$-$C_{50}$)alkyl-O—; —O-phenyl-O—; —O-benzyl-O—; —O—($C_5$-$C_8$)cycloalkyl-O—; —O—($C_1$-$C_{50}$)alkenyl-O—; —O—(CH($CH_3$)—$CH_2$—O)$_n$—; —O—($CH_2$—$CH_2$—O)$_n$—; —O—([CH—$CH_2$—O]$_n$—[$CH_2$—$CH_2$—O]$_m$)$_o$—, where n, m, and o independently of one another denote numbers from 0 to 200; and mixtures thereof.

19. A composition which comprises an oily substance, a surfactant selected from the group consisting of anionic, cationic, nonionic, zwitterionic, amphoteric and mixtures thereof, and from 0.01 to 10% by weight of at least one copolymer obtained by free-radical copolymerization of acryloyldimethyltaurine or acryloyldimethyltaurate or a mixture thereof one or more silicon-containing component capable of free-radical polymerization and having a functionality of at least one and selected from the group consisting of

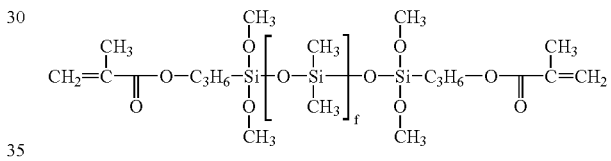

in which f=2 to 500,

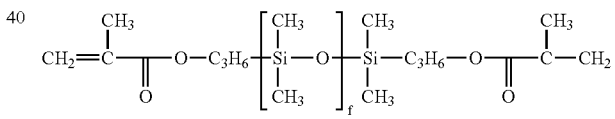

in which f=2 to 500,

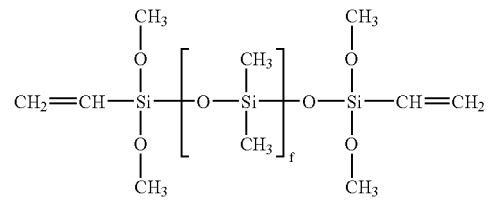

in which f=2-500, and mixtures thereof,
with or in the presence of at least one component selected from the group consisting of:
b) one or more fluorine-containing component capable of free-radical polymerization and having a functionality of at least one,
c) one or more olefinically mono- or polyunsaturated, macromonomer each possessing at least one oxygen, nitrogen, sulfur or phosphorus atom and having a number-average molecular weight of greater than or equal to 200 g/mol, the macromonomer not being the silicon-containing component a) or the fluorine-containing component b), d) at least one polymeric additive having number-average molecular weights of from 200 g/mol to $10^9$ g/mol, e) one or more further olefinically unsaturated, noncationic comonomer which have at least one oxygen, nitrogen, sulfur or phosphorus atom and possess a molecular weight of less than 500 g/mol, and f) one or more olefinically unsaturated, cationic comonomer which has at least one oxygen, nitrogen, sulfur or phosphorus atom and possess a molecular weight of less than 500 g/mol, and mixtures thereof.

20. The composition of claim 19, wherein said macromonomer c) is crosslinking.

21. The composition of claim 19, wherein said olefinically unsaturated, noncationic comonomer e) is crosslinking.

* * * * *